United States Patent [19]

Guibert

[11] Patent Number: 4,667,658
[45] Date of Patent: May 26, 1987

[54] THERMOTHERAPY TECHNIQUE

[75] Inventor: Raul Guibert, Simsbury, Conn.

[73] Assignee: Sunset Ltd., Santa Monica, Calif.

[21] Appl. No.: 854,830

[22] Filed: Apr. 23, 1986

Related U.S. Application Data

[63] Continuation of Ser. No. 697,150, Feb. 1, 1985, abandoned, which is a continuation-in-part of Ser. No. 521,262, Aug. 8, 1983, Pat. No. 4,595,008, which is a continuation-in-part of Ser. No. 313,313, Oct. 20, 1981, Pat. No. 4,461,299, which is a continuation-in-part of Ser. No. 274,504, Jun. 16, 1981, Pat. No. 4,398,535.

[51] Int. Cl.$^4$ .............................................. A61F 7/00
[52] U.S. Cl. .................................. 128/24.1; 128/400; 219/364; 219/374
[58] Field of Search ................. 128/24.1, 399, 400, 128/402; 219/364, 373, 374

[56] References Cited

U.S. PATENT DOCUMENTS

| | | | |
|---|---|---|---|
| 608,928 | 8/1898 | Taylor | 219/373 |
| 1,751,754 | 3/1930 | Duershiner | 219/373 |
| 1,914,026 | 6/1933 | Kirk | 128/400 |
| 2,332,639 | 10/1943 | Hudson | 219/364 |
| 2,410,384 | 10/1946 | Lindsay | 219/364 |
| 2,706,988 | 4/1955 | Weber | 219/373 |
| 3,007,473 | 11/1961 | Jackson | 128/400 |
| 3,368,062 | 2/1968 | Gramenius | 219/414 |
| 3,435,247 | 3/1969 | Pfeiffer | 219/364 |
| 3,501,620 | 3/1970 | Sauer | 219/374 |
| 3,846,616 | 11/1974 | Beck | 219/373 |
| 3,846,618 | 11/1974 | Henderlite | 219/373 |
| 4,013,083 | 3/1977 | Helbling | 219/364 |
| 4,110,600 | 8/1978 | Spotts | 219/374 |
| 4,307,286 | 12/1981 | Guibert | 99/447 |
| 4,327,278 | 4/1982 | Tomaro | 219/364 |
| 4,335,726 | 6/1982 | Kolstedt | 128/402 |
| 4,398,535 | 8/1983 | Guibert | 128/399 |
| 4,461,299 | 7/1984 | Guibert | 128/399 |
| 4,595,008 | 6/1986 | Guibert | 128/399 |

FOREIGN PATENT DOCUMENTS

| | | | |
|---|---|---|---|
| 2342618 | 9/1977 | France | 219/364 |
| 904695 | 2/1982 | U.S.S.R. | 128/402 |

Primary Examiner—Clyde I. Coughenour
Attorney, Agent, or Firm—Michael Ebert

[57] ABSTRACT

A technique for applying therapeutic heat to a skin surface area of a patient whose threshold of sensitivity is determined by that temperature level of the heating medium to which the patient is continuously exposed, above which the patient experiences discomfort. In this technique, the skin surface area is exposed to a heating medium whose temperature is at a base level that is well above ambient but no higher than the temperature sensitivity threshold, the temperature of the medium being periodically raised above the base level to create high heat energy pulses whose peaks are much higher than the threshold. The duty cycle of the pulses is such as to allow for internal heat transfer to take place in the region below the exposed area of the patient in the intervals between pulses to an extent preventing an excessive rise in temperature at the skin surface whereby the patient gains the benefit of high heat energy treatment without discomfort or injury.

7 Claims, 4 Drawing Figures

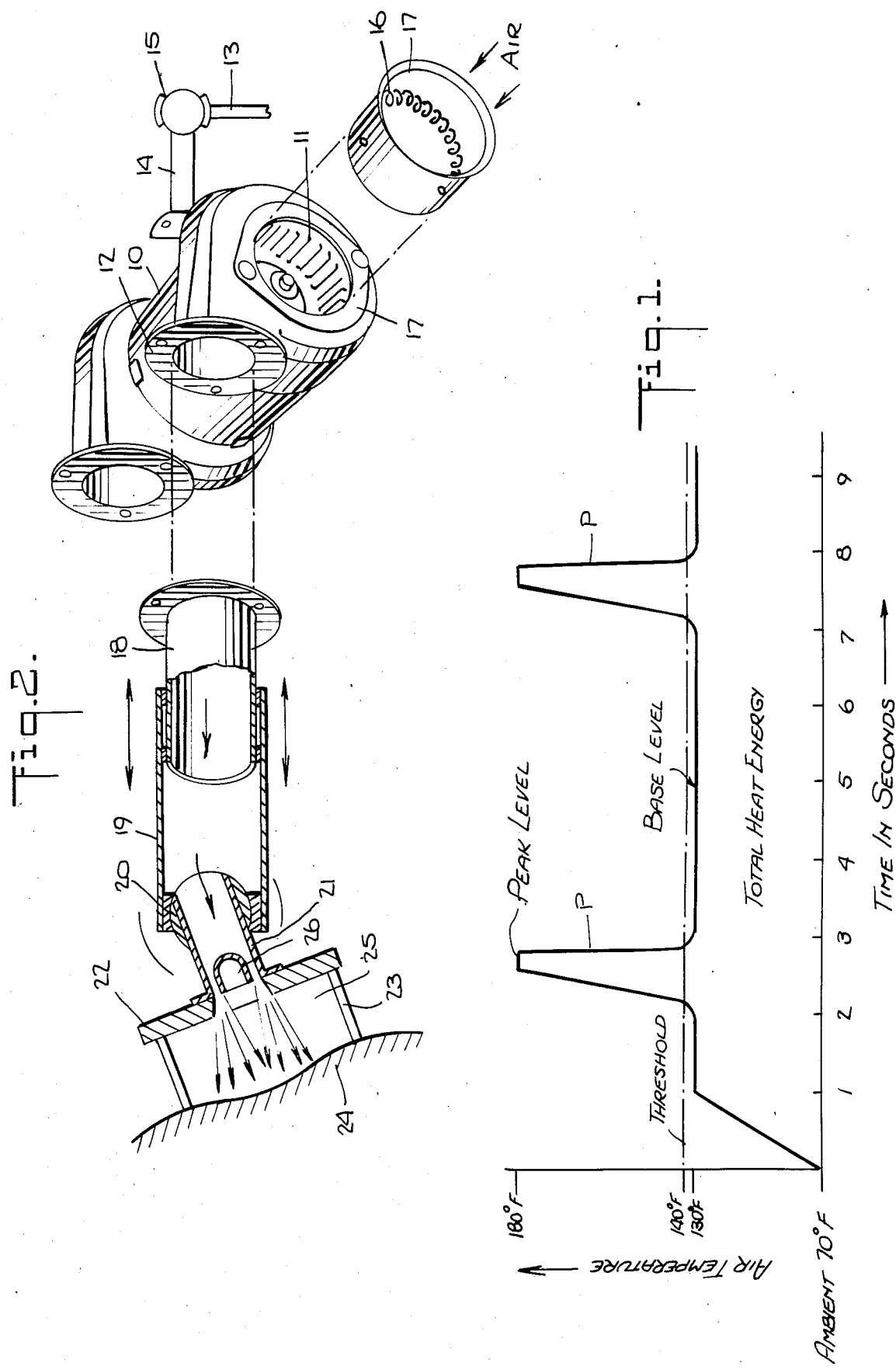

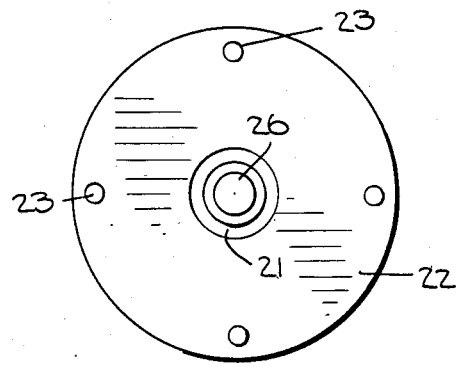
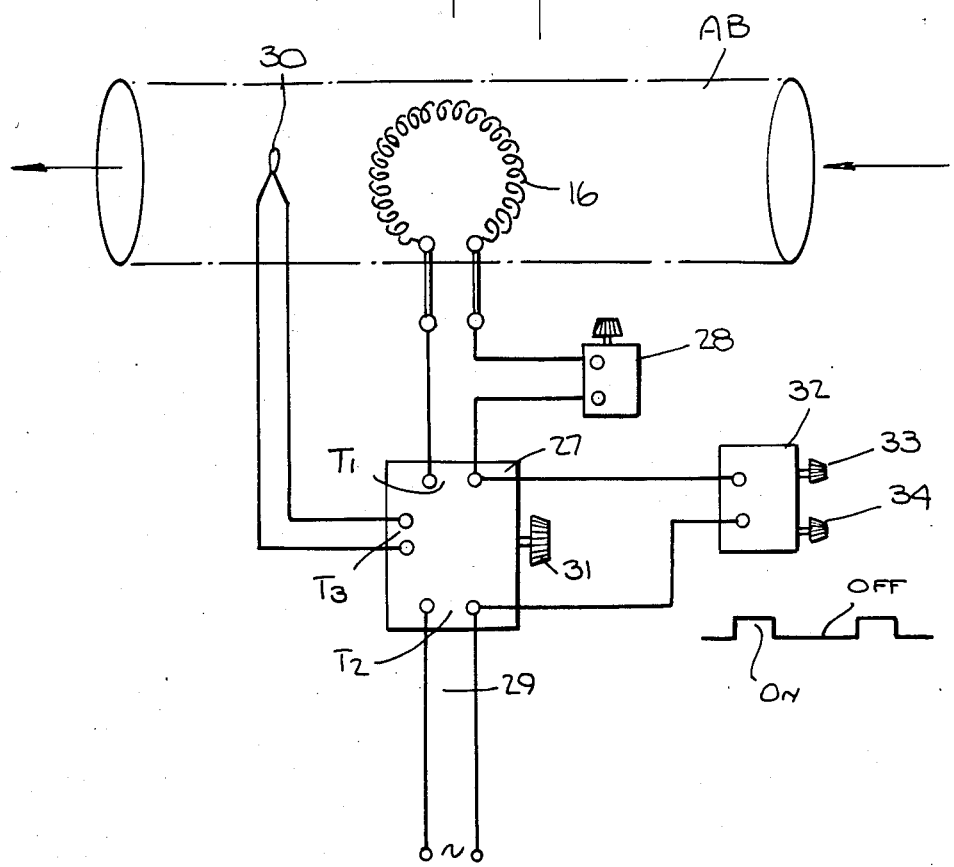

THERMOTHERAPY TECHNIQUE

RELATED APPLICATIONS

This application is a continuation of my copending application Ser. No. 697,150, filed Feb. 1, 1985, now abandoned which is a continuation-in-part of my copending application Ser. No. 521,262, filed Aug. 8, 1983, now U.S. Pat. No. 4,595,008, entitled "Localized Thermotherapy Technique," which copending application is a continuation-in-part of my earlier-filed application Ser. No. 313,313, filed Oct. 20, 1981, now U.S. Pat. No. 4,461,299, which in turn is a continuation-in-part of my still earlier filed application Ser. No. 274,504, filed June 16, 1981, now U.S. Pat. No. 4,398,535, the entire disclosures of these related cases all being incorporated herein by reference.

BACKGROUND OF INVENTION

1. Field of Invention

This invention relates generally to thermotherapy, and in particular to a thermotherapy technique and an instrument based thereon in which the heating medium in a preferred embodiment is a continuous stream of heated air projected at high velocity toward a skin surface area on the body of a patient in a pulsatory heat energy pattern causing rapid inward heat transfer to take place toward an internal problem region underlying this area in a manner raising the temperature of this region without, however, causing undue discomfort or injury to the patient.

2. Prior Art

The term "problem region" as used herein refers to a tumor, a set of muscles, or any other site underlying the skin which is causing difficulty and which lends itself to treatment by hot or cold therapy.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing.

If the heat produced by a body surpasses heat losses therefrom, this gives rise to fever; but if heat losses exceed heat production, then the body temperature falls below the nominal value, resulting in shivering and hypothermia.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a warmed substance; that is, by conduction, or by radiating energy into the body.

Difficulty has heretofore been experienced in effectively applying heat which is electrically or otherwise generated to a patient. When transferring heat inwardly through living tissue to a problem region underlying the skin, if the heat applied to the skin surface is within a tolerable temperature range, then not enough heat energy is transferred to this site to afford beneficial effects.

As pointed out in chapter 10, "Therapeutic Heat" in the text *Therapeutic Heat and Cold*, edited by Justus F. Lehmann and published in 1982 by Williams and Wilkins, it is generally accepted that heat produces desirable therapeutic effect, for it increases the extensibility of collagin tissues, it decreases joint stiffness, and it affords pain relief. Moreover, heat relieves muscular spasms, it aids in the resolution of inflammatory infiltrates, edema and exudates, and it enhances blood flow.

As indicated in the Lehmann text, superficial heat is commonly tied with various forms of heating media such as a paraffin bath, hot air or hot water and radiant heat (infrared). For a given patient, the temperature sensitivity threshold is that temperature level of the heating medium to which the patient is exposed, above which the patient experiences undue discomfort. Thus temperature levels of the medium below the sensitivity threshold are more or less tolerable, whereas those above the threshold are effectively intolerable. If, for example, a patient being subjected to thermotherapy finds that the heat is more than he can stand and wishes to procedure discontinued, clearly the heat of the medium to which he is exposed is above his sensitivity threshold.

One must bear in mind that the temperature sensitivity threshold is determined on the basis of continuous exposure to the heating medium, for one can tolerate much higher heat levels when one is only exposed momentarily or intermittently to high temperatures.

The temperature sensitivity threshold depends on the nature of the heating medium. Thus, as noted in the Lehmann text, when the medium is hot water which is at the same temperature and is applied to the patient in the same fashion as heated paraffin which has a low heat capacity, the paraffin can be tolerated by a patient but the hot water is intolerable for it has a high specific heat and a high order of thermal conductivity.

As a consequence, with conventional heating techniques, regardless of the medium used, when the patient is continuously exposed to a heating medium which is at a substantially constant temperature level, though this level is high enough to bring about adequate heat transfer to the problem region underlying the exposed skin, then the skin temperature is usually well above the tolerable level and this may result in extreme discomfort to the patient and even to the burning of tissue.

It is also now recognized that by heating tumors to a higher temperature than the surrounding tissue, the tumor may be caused to shrink and disappear. As noted in *The New York Times* of Apr. 14, 1982 (section C2) in an article on modern approaches to cancer treatment, the effectiveness of heat therapy is based on the fact that cancers have poor circulation and a reduced ability to dissipate heat. "Thus a temperature of more than 113 degrees Fahrenheit could destroy cancer cells while sparing normal tissue." The concern of the present invention is not with the heat treatment of any particular medical condition or problem region, but with a more effective technique therefor. Thus in the case of tumors, the practical problem encountered is that the surface temperature necessary to raise the tumor temperature to the proper level is intolerable.

While the present invention will be described mainly in connection with thermotherapy or hyperthermia, it is to be understood that a technique and apparatus in accordance with the invention is also applicable to hypothermia treatment in which therapeutic effects are gained by cooling an internal problem region.

SUMMARY OF INVENTION

In view of the foregoing, the main object of this invention is to provide a technique and apparatus based thereon which makes possible localized thermotherapy using exceptionally high temperatures without, however, inflicting injury or causing discomfort to the patient.

More particularly, an object of the invention is to provide a technique and an instrument based thereon in which the patient is exposed to pulses of heat energy.

Still another object of the invention is to provide an efficient and reliable thermotherapy instrument usable in medical offices, hospitals and in the home.

Briefly stated, these objects are attained in a technique for applying therapeutic heat to a limited skin surface area of a patient whose temperature sensitivity threshold is determined by that temperature level of the medium to which the patient is continuously exposed above which the patient experiences undue discomfort or injury. In this technique, continuously projected at high velocity toward the surface area is an air stream heated to a base temperature level that is well above ambient yet somewhat below the sensitivity threshold, the temperature of the air stream being periodically raised above its base level to create heat energy pulses having peaks much higher than the threshold. The duty cycle of the pulses is such as to allow for internal heat transfer to take place in the region below the surface area in the body of the patient in the intervals between pulses to an extent preventing a significant rise in skin surface temperature above the threshold.

In an instrument based on this technique, heat is produced by means of an electrical heater element disposed within an air blower whose outlet is orientable to project a continuous air stream at high velocity toward a selected skin area of the patient being treated. The heater is connected through an electronic controller to a high voltage supply which, if applied directly to the element, would result in maximum heat generation. The controller functions to apply a relatively low voltage to the element and is thermostatically regulated to so energize the element as to heat the continuous air stream to the base line and to maintain the temperature of the stream at this level.

A repeat cycle timer is connected in bypass relation to the controller and acts periodically to apply the high voltage from the supply directly to the heater element. The duty cycle of the timer, which is adjustable, is such that during each operative pulse, the maximum heat energy generated by the heater causes a sharp rise in the temperature of the air stream to a peak that is much higher than the sensitivity threshold, internal heat transfer taking place in the intervals between the pulses preventing an undue rise in surface temperature. The invention is applicable to any heating medium which is electrically generated, such as infrared radiant energy.

OUTLINE OF DRAWINGS

For a better understanding of the invention as well as other objects and further features thereof, reference is made to the following detailed description to be read in conjunction with the accompanying drawings, wherein:

FIG. 1 shows the thermal wave pattern created by a technique in accordance with the invention and by the instrument based thereon;

FIG. 2 illustrates the physical form of the instrument;

FIG. 3 is an end view of the applicator included in the instrument; and

FIG. 4 is a schematic circuit diagram of the heater element included in the instrument and its associated electronic control system.

DESCRIPTION OF INVENTION

The Basic Technique

In order to generally demonstrate the value of thermotherapy in the treatment of problem regions, we shall consider the backache, one of the most common of all human afflictions. As noted in the "Book of Back Care", published by the American Medical Association, most of us at some time in our lives suffer from backache.

The back, an extraordinarily complex structure, is composed of bones, cartilage, nerves, blood vessels, and layers upon layers of muscle, each with its own potential for causing trouble. In physical therapy, heat is most often used to help relax tense and spastic back muscles. As indicated in the "Book of Book Care", heat is usually applied to the skin overlying the problem region with hot towels, hot water bottles, electric heating pads, infrared lamps or paraffin baths.

Because in all conventional heat applicators, the heat is applied continuously to the skin area overlying the problem region, this imposes strict limits on the acceptable temperature level. Thus if one seeks to have the heat penetrate more deeply into the body, the temperature at the surface area must be raised to promote more rapid heat transfer, for the higher the differential between the internal and external temperatures, the greater the rate of transfer. But a point is then quickly reached at which the patient is made uncomfortable— for one can only tolerate continuously applied heat whose temperature level is not excessively above body temperature. The temperature sensitivity threshold for a given patient is that temperature level of the heating medium to which the patient is continuously exposed above which the patient experiences serious discomfort.

Because continuous heat therapy techniques, to be completely safe, must operate at a relatively low temperature level not much higher than the sensitivity threshold, they are of limited effectiveness in the treatment of backache and other painful conditions that are relieved by heat.

In a thermotherapy technique in accordance with the invention, heat energy is applied to a limited skin surface area of the patient overlying a problem region, the energy being in the form of a high-velocity continuous air stream to promote rapid heat transfer. The temperature of the air stream is at a substantially constant base level which is well above ambient but somewhat below the sensitivity threshold of the patient. The temperature level of the air stream is caused to rise periodically to a peak well above the sensitivity threshold, such that if the air stream were continuously maintained at this peak even for a few seconds, though it would then act to promote rapid inward heat transfer, it would at the same time cause extreme discomfort and possibly injury to the patient.

In order, therefore, to render the applied heat energy tolerable and at the same time bring about a rapid inward heat transfer from the skin area to the problem region, the heat energy in a technique in accordance with the invention is applied in a pulsatory thermal air wave pattern.

In a technique in accordance with the invention, a continuous stream of air is projected at high velocity toward a limited skin area of the patient being treated. As shown graphically in FIG. 1, the air temperature which is drawn from the atmosphere is initially at ambient (i.e., 70° F.). The air is heated to a constant base temperature level (i.e., 130° F.) which is well above ambient but somewhat below the temperature sensitivity threshold of the patient (i.e., 140° F.).

In FIG. 1, temperature is plotted against time in one second increments. It will be seen that the temperature of this continuous air stream is periodically raised well above its base level by heat energy pulses to a peak level (i.e., 180° F.), which is much higher than the sensitivity threshold.

In the example shown, the duty cycle is such that each pulse P, which has almost a one second duration, is followed by an interval of four seconds in which the air is at its base level temperature.

The resultant pulsatory thermal air weave pattern is such that a stream of hot air at the base temperature level is blown at high velocity toward the localized skin area to impinge thereon and to flow across the area. This continuous stream is periodically raised in temperature to a peak level so that the localized skin area being subjected to treatment is exposed to high temperature heat energy well above the sensitivity threshold for no more than a brief period insufficient to cause discomfort, followed by an interval at the markedly lower base temperature level during which rapid heat transfer takes places through the body tissue toward the problem region. This inward transfer acts to reduce the temperature at the surface to a degree preventing a significant rise thereof above the sensitivity threshold.

The high velocity air stream is effectively a high wind which promotes heat transfer. In order to prevent windburn, the skin subjected thereto is protectively coated with petroleum jelly or a similar viscous product compatible with the skin. This layer also acts to minimize the outward transfer of heat energy from the skin area to the atmosphere.

A technique in accordance with the invention makes it possible to produce a much greater rise in the temperature of an internal problem region underlying a limited skin area subjected to the heat without, however, discomfort to the patient or damage to the tissue being heated. Because the internal heat is significantly higher in temperature than that heretofore obtainable without discomfort or damage, the beneficial effects are far more pronounced.

While it has been known since ancient times that by inducting, as it were, a localized fever in a problem region, one can reduce pain and obtain therapeutic effects, the mechanism by which the heat acts is not fully understood. The theory underlying a technique in accordance with the invention, as presently understood, is based on the reaction of the nervous system to thermal stimuli that is interpreted by the system as representing fever or an abnormal temperature, even though no fever is physiologically produced. As distinguished from conventional techniques, the present technique makes use of temperatures which, if applied continuously, would simulate a localized body fever.

The nervous system is composed of an extensive network and special tissue that controls and correlates the actions and reactions of the body and its adjustment to the environment. The network consists of a brain and spinal cord which together constitute the central nervous system operating in conjunction with a system of the peripheral nerves which carries nerve impulses or signals to and from the central nervous system. The afferent or sensory fibers convey impulses arising from stimulation of the end organs, as by touch or heat, to muscles and other parts of the body that respond to stimulation.

In many areas of the body, the fibers of a sensory nerve cell and those of a motor nerve cell are interlacing, forming a minor nerve center or reflex arc. Thus, when a finger touches a heated object, the finger is withdrawn instantaneously, for the sensory impulse has stimulated the motor impulse in a reflex arc long before the sensing impulse reaches the brain.

It is well known that the nervous system is capable of carrying out emergency procedures. Thus, when an injury occurs to a particular part of the body, the nervous reaction is a swelling of blood cells near the site clearing the way for emergency measures which include tiny phagocyte cells that pour into the area to consume dirt, bacteria, viruses, and dead and injured cells. When, however, the injury is not localized, the capacity of the body is insufficient to provide a reaction capable of coping with a widespread condition.

Because the nervous system acts in response to stimuli to relieve pain, it is now known to use electrical stimulation for this purpose. Thus, in the paper entitled "New Methods for Achieving Pain Control by Transcutaneous Nerve Stimulation" presented to the American Academy of Neurology, Toronto, April, 1976, by Richard L. Steig, it is pointed out that while the physiological basis for the success of such stimulation is poorly understood, the fact remains that the technique holds great clinical promise.

Nerve stimulation by heat at a level well above normal body temperature in a temperature in accordance with the invention is believed to produce a physiological reaction resulting in the swelling of blood vessels, as in an actual localized trauma, and in bringing to the site an enhanced supply of blood and a multitude of cells which function to relieve or remedy the condition at the problem region that resulted in pain.

The present invention differs significantly from prior thermotherapy techniques in that it makes it possible to stimulate the nervous sytem with much higher temperatures than has heretofore been feasible to bring about a beneficial reaction without, however, causing discomfort to the patient or injury to the surface of the local site being treated.

The Instrument

Referring now to FIGS. 2 and 3, an instrument in accordance with the invention includes a twin air blower having a common motor 10 whose armature shaft is coupled at either end to a turbine ring 11. When ring 11 is rotated, it draws air from the atmosphere at ambient temperature and blows it out at high velocity through an outlet coupled to an outlet mounting flange 12. Since the twins are identical, only one unit thereof will be described. It is to be understood that the invention may take the form of a single unit.

The instrument is supported on a stand 13 provided at its upper end with a swivel 15 to which a cantilever arm 14 is attached, the arm extending from the case of motor 10. Thus the instrument may be angled as necessary toward a patient being treated. In practice, an overhead support may be provided for the unit.

Mounted behind an inlet ring 17 on the motor casing is a helical electrical heater coil 16 in a circular form which when energized, acts to heat the air drawn into the blower through the heater circle so that the stream of air discharged therefrom is at an elevated temperature.

Secured to mounting flange 12 is an outlet formed by telescoping inner and outer tubes 18 and 19, which may be extended or retracted as required. Held within the output end of outlet tube 19 by a universal joint 20 is the input pipe 21 of an applicator formed by an annular plate 22 having a series of feet 23 projecting therefrom which engage the skin surface 24 of a patient to provide a free space 25 between the applicator plate and the skin to receive the stream of heated air which impinges on the skin and is deflected thereby outwardly across the skin surface, thereby subjecting the limited area of the surface surrounding the applicator to heat thereby.

Coaxially supported within input pipe and its output end is a cylindrical baffle 26 having a rounded head which intercepts the flow of air in the center of the pipe and forces the air to be ejected in the annular space surrounding the baffle so that the projected air is in the form of a hollow column 27.

Thus, with this arrangement, one may readily angle the instrument relative to its stand 13; one may also extend the telescoping outlet 18, 19; and one may then orient applicator 22 relative to the outlet and thereby dispose the applicator at any desired site on the body of the patient.

The Circuit

FIG. 4 shows the electrical heater element disposed within the air blower which is represented schematically by tube AB through which the ambient air is blown to create a continuous stream of heated air which is projected at high velocity toward the skin surface. Heater element 16 is connected to the output terminals $T_1$ of an electronic controller 27 through a variable resistor or dimmer 28.

Controller 27, which in practice may be a series D-44 temperature-controller manufactured by Westronics, Inc. of Fort Worth, Tex., and has its input terminals connected by line 29 to a high voltage ac supply which, in practice, may be a conventional 110 V or 220 V v. ac power line. Connected to the control terminals $T_3$ of the controller is a thermocouple or thermistor 30 which is placed in the blower AB to sense the temperature of the heated air being projected from the blower. This controller is provided with a set point control knob 31 which is settable to a desired base temperature level.

Thus, applied to heater element 16 is a relatively low voltage whose value is modulated in response to the sensed temperature value to maintain the basic temperature at a substantially constant level. For example, if the supply voltage is 110 V, the voltage applied by the controller to the heater may be about 60 V.

The controller compares the set point temperature with the sensed temperature to provide a deviation signal which acts to vary the voltage applied to the heater element to maintain the desired base temperature level.

Connected in bypass relation between an input and output terminal of the controller is a repeat cycle timer 32, such as the WP-12 series timer manufactured by the Minarik Electric Co., having control knobs 33 and 34 for independently adjusting the on/off timer and hence the duty cycle. Thus the time range may be 1 to 20 seconds for the "off" timer and 1 to 20 seconds for the "on" timer. In order, therefore, to approximate the duty cycle shown in FIG. 4, the timing is adjusted to provide an "on" time of one second, followed by an "off" time of four seconds in each cycle of operation.

When the timer is on, it effectively shuts out the controller so that the full high voltage of the supply or a somewhat lesser amount as determined by the adjustment of variable resistor 28 is applied across the heater element 16.

Thus, each time the timer is on, the dry heat produced by the heater is substantially increased to reach the desired peak level which is well above the base level. The thermal lag of the heater plays a role in the time it takes for the temperature of the air to rise from the base to the peak level. But because the heater is already energized, it takes much less time for this action to occur than it would take if the heater had to go from a cold off state to a hot on state.

While there has been shown and described a preferred embodiment of a pulsatory thermotherapy technique in accordance with the invention, it will be appreciated that many changes and modifications may be made therein without, however, departing from the essential spirit thereof. Thus the same technique may be used by hypotherapy, in which case the base level is below ambient temperature and the peak level is well below the base level.

The invention is applicable to any heating medium that can be electrically generated and controlled. Thus, instead of a heating medium in the form of forced convection, an infrared heater in the form of an incandescent lamp which operates in the infrared region may be used. This lamp is placed within a reflector mounted in an orientable stand so that the infrared radiation may be directed toward the skin site of the patient.

In this case, the infrared lamp or whatever other infrared generator is used, such as quartz element, is energized as in Fig. 4 through a controller 27 coupled to a high voltage power line so that the voltage applied to the lamp is then relatively low to produce the base level of the thermotherapy curve. Controller 27 is periodically bypassed by the repeat cycle timer 32 to apply a high voltage to the lamp to cause the lamp to generate high energy pulses whose peaks are determined by the setting of dimmer 28 in series with the lamp.

I claim:

1. A technique for therapeutically treating a patient with heat derived from a heating medium, said patient having a temperature sensitivity threshold which is determined by that temperature level of the medium above which the patient experiences undue discomfort, said technique comprising the steps of:
    A. continuously exposing a skin surface area of the patient to the medium which is constituted by a continuously flowing stream of air which is blown at high velocity thereacross and maintaining the temperature of the medium at a base level that is above ambient yet somewhat below the sensitivity threshold; and
    B. periodically raising the temperature of the continuously flowing air stream above its base level to create heat energy pulses having peaks much higher than the threshold, the duty cycle of the pulses being such as to allow for internal heat transfer to take place in the region below the skin surface in the intervals between pulses to an extent preventing a significant rise in surface temperature above the threshold.

2. A technique as set forth in claim 1, wherein said base level is about 130° F. and the peaks are at a temperature of about 180° F.

3. A technique as set forth in claim 1, wherein said pulses have a duration of about one second and the intervals therebetween are a multiple thereof.

4. An instrument for applying therapeutic heat to a limited skin surface area of a patient having a temperature sensitivity threshold which is determined by that temperature level of the medium to which the patient is exposed above which the patient experiences undue discomfort, the instrument comprising:
  A. first means to continuously expose a skin surface area of the patient to a heated medium constituted by a continuously flowing stream of air which is blown at high velocity across said surface area and is maintained at a base temperature level that is above ambient yet somewhat below the sensitivity threshold; and
  B. second means to periodically raise the temperature of the continuously flowing air stream above its base level to create heat energy pulses having a peak level much higher than the threshold, the duty cycle of the pulses being such as to allow for internal heat transfer to take place in the region below the skin surface area in the intervals between pulses to an extent preventing a significant rise in surface temperature above the threshold.

5. An instrument as set forth in claim 4, wherein said first means includes an electrical heater to heat the air stream and an electronic controller which is interposed between said electric heater element and a high voltage supply to energize said element with a relatively low voltage which is regulated by means of a sensor placed in the air stream to maintain the temperature thereof at a substantially constant base level.

6. An instrument as set forth in claim 5, wherein said second means is a repeat cycle timer arranged to bypass said controller periodically to apply the high voltage from the supply directly to the heater element in the desired duty cycle.

7. An instrument as set forth in claim 5, wherein said timer has an adjustable "on" period and an adjustable "off" period whereby the duty cycle is adjustable.

* * * * *